United States Patent [19]
Cha

[11] Patent Number: 5,807,582
[45] Date of Patent: Sep. 15, 1998

[54] FINE-BEADED COLESTIPOL HYDROCHLORIDE AND PHARMACEUTICALLY ELEGANT DOSAGE FORMS MADE THEREFROM

[75] Inventor: Dae Yang Cha, Kalamazoo, Mich.

[73] Assignee: Pharmacia & Upjohn Company, Kalamazoo, Mich.

[21] Appl. No.: 289,141

[22] Filed: Aug. 11, 1994

Related U.S. Application Data

[63] Continuation of Ser. No. 74,262, Jun. 9, 1993, abandoned, which is a continuation of Ser. No. 959,512, Oct. 13, 1992, abandoned, which is a continuation of Ser. No. 656,168, filed as PCT/US89/03330, Aug. 7, 1989, abandoned, which is a continuation-in-part of Ser. No. 237,221, Aug. 26, 1988, abandoned.

[51] Int. Cl.$^6$ .............................. A61K 9/14; A61K 9/20
[52] U.S. Cl. .................. 424/489; 424/78.1; 424/78.08; 424/451; 424/464; 424/501; 523/400; 514/951
[58] Field of Search .......................... 424/489, 78.08, 424/78.1, 451, 464, 501; 528/421, 422; 514/951; 523/400

[56] References Cited

U.S. PATENT DOCUMENTS

| | | | |
|---|---|---|---|
| 3,692,895 | 9/1972 | Nelson | 424/78.08 |
| 3,803,237 | 4/1974 | Lednicer | 424/78.08 |
| 4,439,419 | 3/1984 | Vecchio | 424/78.08 |
| 4,631,305 | 12/1986 | Guyer | 424/78.08 |

*Primary Examiner*—Raj Bawa
*Attorney, Agent, or Firm*—Martha A. Gammill

[57] ABSTRACT

The present invention provides for an improvement in the emulsion copolymerization process for the preparation of fine-beaded colestipol hydrochloride (FBCH) wherein the improvement comprises: 1) utilizing a weight ratio of water to polyethylenepolyamine in the process of 1.8 to 3.6 grams per gram, and 2) utilizing a weight ratio of surface active agent or surfactant to polyethylenepolyamine in the process of 1.0 to 3.0 grams per kilogram. The colestipol hydrochloride product thus produced is a novel fine-beaded form of a known pharmaceutical composition, yielding pharmaceutically elegant dosage forms exhibiting increased potency, including non-gritty oral powders and oral tablets. Conventional colestipol hydrochloride was heretofore available in large spherical granules which produced less elegant (gritty) oral suspensions.

16 Claims, No Drawings

FINE-BEADED COLESTIPOL HYDROCHLORIDE AND PHARMACEUTICALLY ELEGANT DOSAGE FORMS MADE THEREFROM

CROSS-REFERENCE TO RELATED APPLICATIONS

The present application is a continuation application of U.S. Ser. No. 08/074,262, filed 9 Jun. 1993, now abandoned; which is a continuation application of U.S. Ser. No. 07/959,512, filed 13 Oct. 1992, now abandoned; which is a continuation of U.S. Ser. No. 07/656,168, filed 25 Feb. 1991, now abandoned; which is the national stage of international application PCT/US89/03330, filed 7 Aug. 1989, which designated the U.S., now abandoned; which is a continuation-in-part of U.S. Ser. No. 07/237,221, filed 26 Aug. 1988, now abandoned.

BACKGROUND OF THE INVENTION

The present invention provides for an improvement in the emulsion polymerization process for the preparation of fine-beaded colestipol hydrochloride (FBCH). The improvement comprises the utilization of a weight ratio of water to polyethylenepolyamine and a ratio of surface active agent or surfactant to the polyethylenepolyamine. The resultant FBCH is a novel composition of matter, capable of being utilized in novel pharmaceutical formulations and methods. In particular, the present invention provides substantially uniformly small, pharmaceutically elegant particles of colestipol hydrochloride, pharmaceutical compositions containing them, and methods for using them to treat hypercholesterolemia in humans. These pharmaceutical compositions include tablets, palatable or non-gritty oral suspensions or powders (flavored or unflavored), and various drug-containing food products having improved palatability.

Colestipol is a basic anion exchange resin described as a high molecular weight copolymer of diethylenetriamine and 1-chloro-2,3-epoxypropane (epichlorohydrin), with approximately one out of 5 amine nitrogens protonated. It is a light yellow resin which is hygroscopic and swells when placed in water or aqueous fluids. See Merck Index (Tenth Edition) #2440, page 2438. Colestipol hydrochloride is commercially available in granule form as COLESTID® Granules. See Physicians Desk Reference (PDR) 42nd Ed., p. 2119 (1988).

COLESTID® Granules are marketed as a hyperlipidemia agent for oral use. COLESTID® Granules are tasteless and odorless, although they may have a pronounced gritty texture when suspended in liquids consumed orally.

Cholesterol is the major, and probably the sole, precursor of bile acids. During normal digestion, bile acids are secreted via the bile from the liver and gall bladder into the intestines. Bile acids emulsify the fat and lipid materials present in food, thus facilitating absorption. A major portion of the bile acids secreted is reabsorbed from the intestines and returned via the portal circulation to the liver, thus completing the enterohepatic cycle. Only very small amounts of bile acids are found in normal serum. Physicians' Desk Reference (P.D.R.) 42nd Edition, 1988, page 2115.

Colestipol hydrochloride, e.g., COLESTID® Granules, is indicated as adjunctive therapy to diet for the reduction of elevated serum cholesterol in patients with primary hypercholesterolemia (elevated low density lipoproteins).

Heretofore the only known form of colestipol hydrochloride was the granulated form, specifically COLESTID® Granules, which consist of spherical beads of colestipol hydrochloride wherein at least 75% of the particles by weight or volume are greater than 100 microns in diameter and at least 30% of the particles are greater than 80 microns in diameter. These granules must be consumed orally and typically require admixture with a pleasant tasting vehicle at the time of oral consumption. COLESTID® Granules are greater than 99.5% colestipol hydrochloride by weight. The typical daily dose of COLESTID® Granules employed for anti-hyperocholesterolemia varies from 15 to 30 grams per day. Patients taking this medication ordinarily must continue to take anti-cholesterolemic drugs throughout their lives to maintain reduced serum cholesterol levels.

The heretofore known form of colestipol hydrochloride, i.e., COLESTID® Granules, is not well tolerated by patients since the gritty texture of the product is objectionable, severely compromising the pharmaceutical elegance and patient acceptance. Further, the use of a granule formulation means that the drug must be mixed with a liquid vehicle at the time of consumption, an inconvenience for many patients. For example, in order to take this drug, patients must measure the powder, disperse it in a liquid vehicle and drink the entire contents. A pharmaceutically more elegant and convenient dosage form would be a tablet or capsule product.

Previously, no known beaded form of colestipol hydrochloride has had sufficient pharmaceutical elegance and efficacy to provide patients with a fully convenient and effective drug.

DESCRIPTION OF THE PRIOR ART

Large particle size colestipol hydrochloride granules in the form of spherical beads, wherein at least 75% of the particles by weight or volume are greater than 100 microns in diameter and 30% of the particles by weight or volume are greater than 80 microns in diameter, are known. See PDR, supra, page 2115. The use of oral colestipol hydrochloride formulations in spherical bead form to treat hypercholesterolemia is also known. See, e.g., U.S. Pat. No. 3,692,895.

U.S. Pat. No. 3,692,895 claims a method of using colestipol hydrochloride to reduce hypercholesterolemia in humans. It discloses compositions (including tablets and capsules) and processes for reducing hypercholesterolemia in affected mammals and birds. The compositions and processes utilize an orally effective amount of a non-toxic polymer prepared from a polyethylenepolyamine such as tetraethylenepentamine and a bifunctional substance such as epichlorohydrin or 1,2: 3,4-diepoxybutane.

U.S. Pat. No. 4,439,419 discloses a method of using colestipol hydrochloride to neutralize gastric acidity and treat hyperacidity in humans having an excess of gastric acidity and the treatment of ulcers.

U.S. Pat. No. 4,631,305 claims compressed tablets containing a polymeric material such as colestipol hydrochloride as a tablet disintegrating agent. It discloses a tablet containing colestipol hydrochloride in particle size less than 74 microns. However, it does not disclose colestipol hydrochloride wherein the majority of the particles are less than about 50 microns in size, as does the present invention.

Copending PCT application, S.N. PCT/US89/02187, filed 24 May 1989, discloses a fine-milled, non-spherical form of colestipol hydrochloride.

A preferred method for preparing colestipol hydrochloride for medical use is disclosed in U.S. Pat. No. 3,803,237 and is known as the "bead process." The process involves (a) dispersing, by mechanical agitation an aqueous solution of a polyethylenepolyamine, such as diethylenetriamine, and a surface active agent or surfactant, such as sodium alkylbenzene sulfonate (wherein the alkyl portion is from 10 to 18 carbon atoms) in a hydrophobic solvent, such as toluene; (b) adding a bifunctional substance, such as epichlorohydrin, to the dispersion in (a); (c) heating the resultant mixture from (b) for a period of about one to 5 hours; (d) treating the reaction mixture from (c) with an aqueous solution of an alkali metal hydroxide, such as sodium hydroxide, and (e) recovering the copolymer from the reaction mixture in (d) by conventional distillation methods.

In the bead process, disclosed in U.S. Pat. No. 3,803,237, the ratio of water to polyethylenepolyamine can vary from about 1.5:1 to 6.0:1 by weight, preferably about 4.0:1. The amount of surface active agent or surfactant ranges from about 0.3 grams to 12.0 grams for each kilogram of polyethylenepolyamine used in the reaction.

The process of U.S. Pat. No. 3,803,237 is used to make COLESTID® Granules in the form of spherical beads particles, wherein at least 75% of the particles by weight or volume are greater than 100 microns in diameter and 30% of the particles by weight or volume are greater than 80 microns in diameter, are known having the size characteristics noted above. Until the present invention, to the extent colestipol hydrochloride granules smaller than 63 microns were accidentally prepared during commercial production, they were screened out and discarded. A composition of matter comprising substantially uniformly small beads of colestipol hydrochloride has heretofore never been prepared.

SUMMARY OF THE INVENTION

The present invention particularly provides:

(1) In a process for preparing colestipol hydrochloride, a cross-linked copolymerization product of (A) a polyethylenepolyamine containing from about 2 to about 10 ethylene units and having a molecular weight of from about 103 to an average molecular weight of about 450 and (B) 1-chloro-2,3-epoxypropane (epichlorohydrin), wherein said product contains by weight from about 10% to about 47% of said epichlorohydrin which comprises:

(I) dispersing with mechanical agitation an aqueous solution of said polyethylenepolyamine (A) and an alkali metal salt of an alkylbenzenesulfonic acid wherein the alkyl group has from 10 to 18 carbon atoms, inclusive, (i.e., a surface active agent or surfactant) in a hydrophobic solvent selected from the group consisting of aromatic hydrocarbons and chlorinated hydrocarbons, the weight ratio of water to the polyethylenepolyamine being from 1.5:1 to 6.0:1 and the volumetric ratio of hydrophobic solvent to water being from 3.0:1 to 13.0:1;

(II) adding a said member (B) to the dispersion, the molar ratio of the polyethylenepolyamine to the member being from 1:6.0 to 1:1.3;

(III) heating the resulting mixture for one to 5 hours at a temperature of 40° C. to 100° C.;

(IV) treating the heated mixture with an aqueous solution an alkali metal hydroxide;

and (V) recovering the bead form of cross-linked copolyerization product; the improvement which comprises:

i) utilizing a weight ratio of water to polyethlenepolyamine of 1.8 to 3.6 grams per gram; and ii) utilizing a weight ratio of surface active agent or surfactant to polyethylenepolyamine of 1.0 to 3.0 grams per kilogram;

(2) The above improvement wherein the weight ratio of water to polyethylenepolyamine is 2.2 grams per gram and the weight ratio of surface active agent or surfactant to polyethylenepolyamine is 2.5 grams per kilogram;

(3) a composition of matter consisting essentially of fine-beaded colestipol hydrochloride (FBCH);

(4) FBCH wherein greater than 95% of the particles are spherical, non-aggregated particles, greater than 75% of the particles (by weight or volume) are smaller than almost 50 microns in diameter and greater than 35% of the particles (by weight or volume) are less than about 45 microns in diameter;

(5) FBCH in a pharmaceutical unit dosage form;

(6) FBCH in tablet, or capsule form;

(7) FBCH in tablet containing about 500 mg of drug;

(8) in the method of treating hypercholesterolemia in a patient by administering a pharmaceutical composition containing colestipol hydrochloride, the improvement characterized by use of fine-beaded colestipol hydrochloride (FBCH) in said composition;

(9) the above improvement wherein a known cholesterol-lowering agent, such as a 3-hydroxy-3-methylglutaryl coenzyme A reductase inhibitor of gemfibrozil (LOPID) is administered concomitantly; and

(10) a food product containing a concentration of FBCH effective to treat hypercholesterolemia when a predetermined quantity of said product is consumed.

The invention thus provides for an improvement in the emulsion polymerization process for the preparation of fine-beaded colestipol hydrochloride (FBCH). Surprisingly and unexpectedly, it has been found that by selecting the ranges of water and surfactant levels claimed herein, substantially uniformly small beads of colestipol hydrochloride are obtained. The resultant FBCH is a novel composition of matter, capable of being utilized in novel pharmaceutical formulations and methods. In particular, the present invention provides substantially uniformly small, pharmaceutically elegant particles of colestipol hydrochloride, pharmaceutical compositions containing them, and methods for using them to treat hypercholesterolemia in humans. These pharmaceutical compositions include tablets, palatable or non-gritty oral suspensions or powders (flavored or unflavored), and various drug-containing food products having improved palatability.

By "fine-beaded" is meant a substantially spherical form of colestipol hydrochloride (greater than 95% spherical, non-aggregated particles, most preferably greater than about 99% spherical particles) wherein greater than about 75% of the particles, by weight or volume, are less than about 50 microns in diameter and greater than about 35% of the particles (as a proportion of their total weight or volume), are less than about 45 microns in diameter. These particle size measurements were determined by standard light-scattering assay techniques.

By "pharmaceutical unit dose" is meant a discrete quantity of FBCH in a form suitable for administering for medical purposes. Thus, an ideal unit dose would be one wherein one unit, or an integral amount thereof (e.g., one or more packets each containing a predetermined amount of FBCH) contains a safe and effective dose for lowering serum cholesterol. As would be apparent to a person of ordinary skill in pharmaceutical formulations, the fine-beaded colestipol hydrochloride (FBCH) of the present invention can be formulated into conventional tablets for oral administration, optionally utilizing known tablet excipients, e.g., binders, fillers, and the like.

By "surfactant or surface active agent" is meant the alkali metal salts, ie, sodium, lithium, or potassium salts, of alkylarylsulfonic acids wherein the alkyl group of said acid has from 10 to 18 carbon atoms, inclusive, or a mixture of the same. Illustrative of the surface active agents or surfactants that can be used are sodium decylbenzenesulfonate, sodium dodecylbenzenesulfonate, potassium tridecylbenzenesulfonate, sodium octadecylbenzenesulfonate, and the like.

The fine-beaded colestipol hydrochloride (FBCH) of this invention is most preferably prepared by the emulsion polymerization "bead process", wherein the improvement comprises the utilization of the following process conditions from the ranges disclosed in U.S. Pat. No. 3,803,237:

i) utilizing a weight ratio of water to polyethylenepolyamine of 1.8 to 3.6 grams per gram, most preferably at 2.2 grams per gram, out of a range of 1.5:1 to 6.0:1 grams per gram, and ii) utilizing a weight ratio of surface active agent or surfactant to polyethylenepolyamine of 1.0 to 3.0 grams per kilogram, most preferably at 2.5 grams per kilogram, out of the range of 0.3 to 12.0 grams per kilogram.

Surprisingly and unexpectedly, the FBCH produced by the improved process of this invention is a free-flowing powder, consisting essentially of substantially uniformly small, spherical particles of colestipol hydrochloride.

Microscopic examination of the FBCH produced from the improved process of this invention shows that nearly all particles are spherical with a small number of aggregated particles that are dumbbell-shaped. Essentially all particles range in size from 30–65 microns. FBCH powder is ideally suited for incorporation into a number of pharmaceutical dosage forms and food products.

Surprisingly and unexpectedly, the novel form of colestipol hydrochloride of the present invention is more potent than the conventional large particle size spherical beads of the prior art, allowing for more convenient oral administration, utilizing less frequent and/or lower doses of the drug. The potency of FBCH in quail was found to have increased an average of three-fold as compared to conventional colestipol hydrochloride granules. Moreover, because this increased potency is coupled with the ability to produce in oral tablets, the present invention provides a surprisingly and unexpectedly more elegant and convenient pharmaceutical product.

Thus, in hyperlipidemic patients with serum cholesterol values above 200 mg per 100 ml, the composition of the present invention effectively lowers cholesterol levels when the daily dose of FBCH varies from about 3 to about 12 gm, administered from one to three times daily. Unexpectedly, therefore, the present invention provides the opportunity for conveniently dosing a patient with higher potency tablets before each meal.

FBCH can be combined with other known cholesterol lowering agents to provide further lowering of serum cholesterol, triglyceride, and LDL cholesterol values. Such agents include, e.g., MEVACOR®, niacin, LOPID® or LORELCO®.

The FBCH is adaptable to making a flavored dry mix which is constituted into a flavored beverage by simply adding water. These flavored mixes typically contain a viscosity inducing agent such as a gum or a low molecular weight synthetic polymer; flavoring agents such as sucrose, aspartame or sodium saccharin; colorants; wetting agents or surfactants such as dioctyl sodium sulfosuccinate or sodium lauryl sulfate; agents to provide tartness and control acidity such as citric acid, ascorbic acid, potassium citrate or sodium citrate; flavorants such as lemon or orange; and preservatives such as BHA. Similarly, it can be used as an additive to powdered food products, including pudding and pie filling mixes, gelatin, cake mixes, powdered eggs and powdered potatoes, instant breakfast drinks, gravies and sauces (e.g., Hollandaise), prepared cereal products (oatmeal, cream of wheat, hominy grits), and drink mixes (powdered fruit punches, powdered fruit drinks). Likewise, FBCH can be used in prepared foods themselves; for example, it can be used as an additive in cakes, pasta products, candy, cookies, confections, yogurts, including frozen yogurt products, ice cream and ice cream products and prepared meats (hamburger, sausages and the like).

DESCRIPTION OF THE PREFERRED EMBODIMENTS

Example 1 Preparation of Fine-beaded Colestipol Hydrochloride

The reaction vessel is a five liter, three-necked round bottom flask with four side-wall baffles, equipped with a heating mantel, cold-water reflux condenser, distillation condenser, and a 4.5-inch impeller.

Into the reaction vessel is introduced 1,237 milliliters of toluene, 283 milliliters of de-ionized (by reverse osmosis) water, 1.70 milliliters of Witconate 60B Stock solution (prepared by diluting Witconate 60B 2.9:1), and 135.7 milliliters of diethylenetriamine at room temperature. This initial charge is agitated at 350 revolutions-per-minute with the reflux condenser on and heated to a temperature range of 78° C. to 82° C. When this temperature range is achieved, the heating mantel is removed and 186 milliliters of epichlorohydrin is added over a 45 minute period, Addition of epichlorohydrin begins the polymerization and the reaction mixture becomes milky-white in color and then changes slowly to a more clear slurry of water-swollen polymer beads in toluene. The heat of reaction produces an exotherm that raises the temperature of the reaction mixture to its boiling point. When the boiling subsides, the heating mantel is returned to maintain a refluxing temperature of 85° C. When epichlorohydrin addition is complete, the mixture is stirred for 3 hours at the refluxing temperature (cook-down).

After the cook-down, 91.2 milliliters of 50 percent sodium hydroxide solution is added over a 10 minute period. The distillation condenser is turned on. Heating is resumed to remove the water produced by the reaction mixture and to cure the polymer. The water distilled off is to be replaced with an equal volume of toluene in order to maintain the volume in the reactor. This distillation process requires up to 4 hours. Continue refluxing for an additional 5 hours in order to cure the polymer. The reaction mixture is then cooled to below 90° C. and 842 milliliters of de-ionized water is added.

The toluene added during the water distillation is also removed by distillation. First, a volume of water equal to the amount of distillate collected is added to maintain a constant volume in the reactor. The reaction vessel is heated to maintain a refluxing temperature of 85° C. and requires approximately 5 hours. After toluene distillation, the reaction mixture is first cooled with cold water; then, the mixture is cooled over an ice bath to room temperature The reaction mixture is filtered through a polyester-cloth ceramic filter that is 20 centimeters in diameter and 7 centimeters in height. The filter cake is washed with two 500 milliliter rinses of de-ionized water. The cake is then slurried with 1,250 milliliters of de-ionized water and filtered again as above described. Finally, the cake is again slurried with 1,250 milliliters of de-ionized water, but is rinsed this time with two 500 milliliters of de-ionized water. The resultant wet cake yields approximately 1,160 grams.

The wet cake is dried in a vacuum oven at 50° C. to a constant weight to yield 260 grams of FBCH.

I claim:

1. In a process for preparing colestipol hydrochloride, a cross-linked copolymerization product of (A) a polyethylenepolyamine containing from about 2 to about 10 ethylene units and having a molecular weight of from about 103 to an average molecular weight of about 450 and (B) epichlorohydrin, wherein the product contains by weight from about 10% to about 47% of the epichlorohydrin which comprises the following steps performed sequentially:

(I) dispersing with mechanical agitation an aqueous solution of the polyethylenepolyamine (A) and a surfactant that is an alkali metal salt of an alkylbenzenesulfonic acid wherein the alkyl group has from 10 to 18 carbon atoms, inclusive, the weight ratio of surfactant to polyethylenepolyamine being from 0.3:1000 to 12:1000, in a hydrophobic solvent selected from the group consisting of aromatic hydrocarbons and chlorinated hydrocarbons, the weight ratio of water to the polyethylenepolyamine being from 1.5:1 to 6.0:1 and the volumetric ratio of hydrophobic solvent to water being from 3.0:1 to 13.0:1;

(II) adding the epichlorohydrin to the dispersion, the molar ratio of the polyethylenepolyamine to epichlorohydrin being from 1:6.0 to 1:1.3;

(III) heating the resulting mixture for one (1) to five (5) hours at a temperature of 40° C. to 100° C.;

(IV) treating the heated mixture with an aqueous solution of an alkali metal hydroxide; and (V) recovering the bead form of the colestipol hydrochloride wherein greater than 95% of the particles are spherical particles and wherein the majority of the particles are less than about 63 microns in size;

the improvement which comprises:

i) utilizing a weight ratio of water to polyethylenepolyamine of 1.8 to 3.6 grams per gram; and ii) utilizing a weight ratio of surfactant to polyethylenepolyamine of 1.0 to 3.0 grams per kilogram.

2. The improvement according to claim 1 wherein the majority of the particles of colestipol hydrochloride are less than about 50 microns in size.

3. The improvement according to claim 1 which further comprises: iii) heating the dispersion of step (I) to 78° to 82° C. prior to proceeding with step (II).

4. The improvement according to claim 1 wherein the water to polyethylenepolyamine weight ratio is 2.2 grams per gram and the surfactant to polyethylenepolyamine weight ratio is 2.5 grams per kilogram.

5. Colestipol hydrochloride in bead form, obtainable by the process of claim 1, wherein greater than 75% of the particles by weight or volume are smaller than almost 50 μm in diameter and greater than 35% of the particles by weight or volume are less than about 45 μm in diameter.

6. Colestipol hydrochloride according to claim 5 wherein greater than 99% of the particles are spherical particles.

7. An anti-hypercholesteremic pharmaceutical composition, in unit dose form, comprising colestipol hydrochloride according to claim 5.

8. A composition according to claim 7, in tablet, packet or capsule form.

9. A composition according to claim 8, in the form of a 500 mg tablet.

10. An oral composition comprising colestipol hydrochloride according to claim 5 and another cholesterol-lowering agent selected from the group consisting of a 3-hydroxy-3-methylglutaryl coenzyme A reductase inhibitor, gemfibrozil, niacin and probucol, for concomitant use in treating hypercholesterolemia.

11. A composition according to claim 10, wherein the cholesterol-lowering agent is a 3-hydroxy-3-methylglutaryl coenzyme A reductase inhibitor.

12. A food product comprising colestipol hydrochloride according to claim 5.

13. In the method of treating hypercholesterolemia in a patient by administering colestipol hydrochloride, the improvement characterized by using colestipol hydrochloride according to claim 5 as the active ingredient therewithin.

14. The improvement according to claim 13 wherein colestipol hydrochloride is administered concomitantly with another cholesterol lowering agent selected from the group consisting of a 3-hydroxy-3-methylglutaryl coenzyme A reductase inhibitor, gemfibrozil, niacin and probucol.

15. The improvement of claim 14, wherein the cholesterol lowering agent is a 3-hydroxy-3-methylglutaryl coenzyme A reductase inhibitor.

16. A food product containing a concentration of colestipol hydrochloride according to claim 5 effective to treat hypercholesterolemia when a unit dose of said product is consumed.

* * * * *